(12) United States Patent
Labrecque et al.

(10) Patent No.: US 8,001,922 B2
(45) Date of Patent: Aug. 23, 2011

(54) APPLICATION OF A COATING ON A MEDICAL DEVICE

(75) Inventors: Roger Labrecque, Londonderry, NH (US); Geoffrey Moodie, Hudson, NH (US); Joseph Ferraro, Londonderry, NH (US); Lisa Rogers, Londonderry, NH (US); Paul Martakos, Pelham, NH (US); Theodore Karwoski, Hudson, NH (US); Steve A. Herweck, Nashua, NH (US); Suzanne Conroy, Dracut, MA (US); Brian Sunter, Londonderry, NH (US); Georgette Henrich, Dracut, MA (US)

(73) Assignee: Atrium Medical Corporation, Hudson, NH (US)

( * ) Notice: Subject to any disclaimer, the term of this patent is extended or adjusted under 35 U.S.C. 154(b) by 592 days.

(21) Appl. No.: 11/238,554

(22) Filed: Sep. 28, 2005

(65) Prior Publication Data
US 2006/0121081 A1    Jun. 8, 2006

Related U.S. Application Data

(60) Provisional application No. 60/613,745, filed on Sep. 28, 2004.

(51) Int. Cl.
*B05C 1/00* (2006.01)
(52) U.S. Cl. .......................... 118/200; 427/2.1; 427/2.24
(58) Field of Classification Search ................ 118/500
See application file for complete search history.

(56) References Cited

U.S. PATENT DOCUMENTS

| | | | |
|---|---|---|---|
| 3,556,294 A * | 1/1971 | Walck et al. | .......... 206/210 |
| 3,967,728 A | 7/1976 | Gordon et al. | |
| 4,323,547 A | 4/1982 | Knust et al. | |
| 4,814,329 A | 3/1989 | Harsanyi et al. | |
| 4,847,301 A | 7/1989 | Murray | |
| 4,894,231 A | 1/1990 | Moreau et al. | |
| 4,952,419 A | 8/1990 | De Leon et al. | |
| 5,151,272 A | 9/1992 | Engstrom et al. | |
| 5,371,109 A | 12/1994 | Engstrom et al. | |
| 5,403,283 A | 4/1995 | Luther | |
| 5,464,650 A | 11/1995 | Berg et al. | |
| 5,509,899 A | 4/1996 | Fan et al. | |
| 5,579,149 A | 11/1996 | Moret et al. | |

(Continued)

FOREIGN PATENT DOCUMENTS

EP    0623354 B1    11/1994

(Continued)

OTHER PUBLICATIONS

A paper entitled, "Evaluation of the Biocompatibility and Drug Delivery Capabilities of Biological Oil Based Stent Coatings," by Li, Shengqiao of the Katholieke Universiteit Leuven.

(Continued)

*Primary Examiner* — Dah-Wei D Yuan
*Assistant Examiner* — Robert S Walters, Jr.
(74) *Attorney, Agent, or Firm* — Morse, Barnes-Brown & Pendleton, P.C.; Sean D. Detweiler, Esq.

(57) ABSTRACT

Devices for the provision of a coating on an implantable medical device are provided. The coating includes a bio-absorbable carrier component. In addition to the bio-absorbable carrier component, a therapeutic agent component can also be provided. The devices provide a coating having improved uniformity and coverage which in turn allow for greater control of the amount and dosage of the coating.

13 Claims, 9 Drawing Sheets

U.S. PATENT DOCUMENTS

| | | | |
|---|---|---|---|
| 5,591,230 | A | 1/1997 | Horn et al. |
| 5,637,113 | A | 6/1997 | Tartaglia et al. |
| 5,700,286 | A | 12/1997 | Tartaglia et al. |
| 5,753,259 | A | 5/1998 | Engstrom et al. |
| 5,874,470 | A | 2/1999 | Nehne et al. |
| 5,906,831 | A | 5/1999 | Larsson et al. |
| 5,955,502 | A | 9/1999 | Hansen et al. |
| 6,005,004 | A | 12/1999 | Katz et al. |
| 6,077,698 | A | 6/2000 | Swan et al. |
| 6,083,950 | A | 7/2000 | Anand et al. |
| 6,090,809 | A | 7/2000 | Anand et al. |
| 6,117,911 | A | 9/2000 | Grainger et al. |
| 6,146,358 | A | 11/2000 | Rowe |
| 6,152,944 | A | 11/2000 | Holman et al. |
| 6,193,746 | B1 | 2/2001 | Strecker |
| 6,197,357 | B1 | 3/2001 | Lawton et al. |
| 6,206,916 | B1 | 3/2001 | Furst |
| 6,211,315 | B1 | 4/2001 | Larock et al. |
| 6,228,383 | B1 | 5/2001 | Hansen et al. |
| 6,229,032 | B1 | 5/2001 | Jacobs et al. |
| 6,245,811 | B1 | 6/2001 | Horrobin et al. |
| 6,254,634 | B1 | 7/2001 | Anderson et al. |
| 6,262,109 | B1 | 7/2001 | Clark et al. |
| 6,273,913 | B1 | 8/2001 | Wright et al. |
| 6,284,268 | B1 | 9/2001 | Mishra et al. |
| 6,299,604 | B1 | 10/2001 | Ragheb et al. |
| 6,331,568 | B1 | 12/2001 | Horrobin |
| 6,358,556 | B1 | 3/2002 | Ding et al. |
| 6,364,893 | B1 | 4/2002 | Sahatjian et al. |
| 6,369,039 | B1 | 4/2002 | Palasis et al. |
| 6,387,379 | B1 | 5/2002 | Goldberg et al. |
| 6,410,587 | B1 | 6/2002 | Grainger et al. |
| 6,444,318 | B1 | 9/2002 | Guire et al. |
| 6,451,373 | B1 | 9/2002 | Hossainy et al. |
| 6,465,525 | B1 | 10/2002 | Guire et al. |
| 6,471,980 | B2 | 10/2002 | Sirhan et al. |
| 6,491,938 | B2 | 12/2002 | Kunz |
| 6,503,556 | B2 | 1/2003 | Harish et al. |
| 6,527,801 | B1 | 3/2003 | Dutta |
| 6,565,659 | B1 | 5/2003 | Pacetti et al. |
| 6,569,441 | B2 | 5/2003 | Kunz et al. |
| 6,610,035 | B2 | 8/2003 | Yang et al. |
| 6,641,611 | B2 | 11/2003 | Jayaraman |
| 6,645,547 | B1 | 11/2003 | Shekalim |
| 6,663,880 | B1 | 12/2003 | Roorda et al. |
| 6,670,355 | B2 | 12/2003 | Azrolan et al. |
| 6,677,342 | B2 | 1/2004 | Wolff et al. |
| 6,730,064 | B2 | 5/2004 | Ragheb et al. |
| 6,764,509 | B2 | 7/2004 | Chinn et al. |
| 6,776,796 | B2 | 8/2004 | Falotico et al. |
| 6,833,004 | B2 | 12/2004 | Ishii et al. |
| 6,899,729 | B1 | 5/2005 | Cox et al. |
| 6,918,927 | B2 | 7/2005 | Bates et al. |
| 2001/0025196 | A1 | 9/2001 | Chinn et al. |
| 2002/0007209 | A1 | 1/2002 | Scheerder et al. |
| 2002/0012741 | A1 | 1/2002 | Heinz et al. |
| 2002/0032414 | A1 | 3/2002 | Ragheb et al. |
| 2002/0098278 | A1 | 7/2002 | Bates et al. |
| 2002/0116045 | A1 | 8/2002 | Eidenschink |
| 2002/0120333 | A1 | 8/2002 | Keogh et al. |
| 2002/0122877 | A1* | 9/2002 | Harish et al. ............... 427/2.24 |
| 2003/0003125 | A1 | 1/2003 | Nathan et al. |
| 2003/0004564 | A1 | 1/2003 | Elkins et al. |
| 2003/0069632 | A1 | 4/2003 | De Scheerder et al. |
| 2003/0072784 | A1 | 4/2003 | Williams |
| 2003/0077310 | A1 | 4/2003 | Pathak et al. |
| 2003/0083740 | A1 | 5/2003 | Pathak |
| 2003/0086958 | A1 | 5/2003 | Arnold et al. |
| 2003/0130206 | A1 | 7/2003 | Koziak et al. |
| 2003/0175408 | A1 | 9/2003 | Timm et al. |
| 2003/0176915 | A1 | 9/2003 | Wright et al. |
| 2003/0204168 | A1 | 10/2003 | Bosma et al. |
| 2003/0204618 | A1 | 10/2003 | Foster et al. |
| 2003/0207019 | A1 | 11/2003 | Shekalim et al. |
| 2004/0014810 | A1 | 1/2004 | Horrobin |
| 2004/0039441 | A1 | 2/2004 | Rowland et al. |
| 2004/0137066 | A1 | 7/2004 | Jayaraman |
| 2004/0142094 | A1 | 7/2004 | Narayanan |
| 2004/0167572 | A1 | 8/2004 | Roth et al. |
| 2004/0170685 | A1 | 9/2004 | Carpenter et al. |
| 2004/0224003 | A1 | 11/2004 | Schultz |
| 2004/0230176 | A1 | 11/2004 | Shanahan et al. |
| 2005/0159809 | A1 | 7/2005 | Hezi-Yamit et al. |
| 2005/0182485 | A1 | 8/2005 | Falotico et al. |
| 2005/0187376 | A1 | 8/2005 | Pacetti |
| 2005/0232971 | A1 | 10/2005 | Hossainy et al. |
| 2005/0249775 | A1 | 11/2005 | Falotico et al. |

FOREIGN PATENT DOCUMENTS

| | | |
|---|---|---|
| EP | 0730864 B1 | 9/1996 |
| EP | 0790822 B1 | 8/1997 |
| EP | 0873133 B1 | 10/1998 |
| EP | 0917561 B1 | 5/1999 |
| EP | 1140243 B1 | 10/2001 |
| EP | 1181943 A1 | 2/2002 |
| EP | 1270024 A1 | 1/2003 |
| EP | 1273314 A1 | 1/2003 |
| EP | 1364628 A1 | 11/2003 |
| EP | 1557183 A1 | 7/2005 |
| WO | WO-90/01969 A1 | 3/1990 |
| WO | WO-95/26715 A2 | 10/1995 |
| WO | WO-97/02042 A1 | 1/1997 |
| WO | WO-97/09367 A1 | 3/1997 |
| WO | WO-97/13528 A1 | 4/1997 |
| WO | WO-98/30206 A1 | 7/1998 |
| WO | WO-98/54275 A3 | 12/1998 |
| WO | WO-00/40278 A1 | 7/2000 |
| WO | WO-00/62830 A2 | 10/2000 |
| WO | WO-01/24866 A1 | 4/2001 |
| WO | WO-01/26585 A1 | 4/2001 |
| WO | WO-01/66036 A2 | 9/2001 |
| WO | WO-01/76649 A1 | 10/2001 |
| WO | WO-02/49535 A2 | 6/2002 |
| WO | WO-02/100455 A2 | 12/2002 |
| WO | WO-03/000308 A1 | 1/2003 |
| WO | WO-03/015748 A2 | 2/2003 |
| WO | WO-03/028622 A2 | 4/2003 |
| WO | WO-03/037397 A2 | 5/2003 |
| WO | WO-03/037398 A2 | 5/2003 |
| WO | WO-03/039612 A1 | 5/2003 |
| WO | WO-03/041756 A1 | 5/2003 |
| WO | WO-03/070125 A1 | 8/2003 |
| WO | WO-03/092741 A1 | 11/2003 |
| WO | WO-2004/004598 A2 | 1/2004 |
| WO | WO-2004/006976 A1 | 1/2004 |
| WO | WO-2004/006978 A1 | 1/2004 |
| WO | WO-2005/000165 A1 | 1/2005 |
| WO | WO-2005/016400 A1 | 2/2005 |
| WO | WO-2005/053767 A1 | 6/2005 |

OTHER PUBLICATIONS

International Search Report for Application No. PCT/US05/34836, dated Jul. 6, 2006.

Camurus, "In our endeavors to create the unique, we start with the best. Your product."

Drummond, Calum J. et al, "Surfactant self-assembly objects as novel drug delivery vehicles," *Current Opinion in Colloid & Interface Science*, vol. 4:449-456 (2000).

Engström, Sven, "Drug Delivery from Cubic and Other Lipid-water Phases," *Lipid Technology*, vol. 2(2):42-45 (1990).

Hwang, Chao-Wei et al, "Physiological Transport Forces Govern Drug Distribution for Stent-Based Delivery," *Circulation*, vol. 104:600-605 (2001).

Oberhoff, Martin et al, "Local and Systemic Delivery of Low Molecular Weight Heparin Following PTCA: Acute Results and 6-Month Follow-Up of the Initial Clinical Experience With the Porous Balloon (PILOT-Study)," *Catheterization and Cardiovascular Diagnosis*, vol. 44:267-274 (1998).

Salu, Koen J. et al, "Addition of cytochalasin D to a biocompatible oil stent coating inhibits intimal hyperplasia in a porcine coronary model," *Coronary Artery Disease*, vol. 14(8):545-555 (2003).

Scheller, Bruno et al, "Addition of Paclitaxel to Contrast Media Prevents Restenosis After Coronary Stent Implantation," *Journal of the American College of Cardiology*, vol. 42(8):1415-1420 (2003).

* cited by examiner

APPLICATION OF A COATING ON A MEDICAL DEVICE

RELATED APPLICATIONS

This application claims priority to, and the benefit of, co-pending U.S. Provisional Application No. 60/613,745, filed Sep. 28, 2004, for all subject matter common to both applications. The disclosure of said provisional application is hereby incorporated herein by reference in its entirety. This application also relates to co-pending U.S. patent application Ser. No. 11/236,908, filed concurrently with this application on Sep. 28, 2005.

FIELD OF THE INVENTION

The present invention relates to devices and techniques for applying coatings to medical devices. More specifically, to devices and techniques for applying coatings to medical devices, such as stents, balloons, and catheters. The coatings can be used for delivery of one or more biologically active agents, providing controlled short or long term release of biologically active components from the surface of the medical device.

BACKGROUND OF THE INVENTION

Therapeutic agents may be delivered to a targeted location in a human utilizing a number of different methods. For example, agents may be delivered nasally, transdermally, intravenously, orally, or via other conventional methods. Delivery may vary by release rate (e.g., quick release, slow release, or biphasic release). Delivery may also vary as to how the drug is administered. Specifically, a drug may be administered locally to a targeted area, or administered systemically.

With systemic administration, the therapeutic agent is administered in one of a number of different ways including orally, inhallationally, or intravenously to be systemically processed by the patient. However, there are drawbacks to systemic delivery of a therapeutic agent, one of which is that high concentrations of the therapeutic agent travels to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

An alternative to the systemic administration of a therapeutic agent is the use of a targeted local therapeutic agent delivery approach. With local delivery of a therapeutic agent, the therapeutic agent is administered using a medical device or apparatus, directly by hand, or sprayed on the tissue, at a selected targeted tissue location of the patient that requires treatment. The therapeutic agent emits, or is otherwise delivered, from the medical device apparatus, and/or carrier, and is applied to the targeted tissue location. The local delivery of a therapeutic agent enables a more concentrated and higher quantity of therapeutic agent to be delivered directly at the targeted tissue location, minimizing or eliminating broader systemic side effects. With local delivery, the therapeutic agent that escapes the targeted tissue location dilutes as it travels to the remainder of the patient's body, substantially reducing or eliminating systemic effects.

Local delivery is often carried out using a medical device as the delivery vehicle. One example of a medical device that is used as a delivery vehicle is a stent. Boston Scientific Corporation sells the Taxus® stent, which contains a polymeric coating for delivering Paclitaxel. Johnson & Johnson, Inc. sells the Cypher® stent which includes a polymeric coating for delivery of Sirolimus.

Targeted local therapeutic agent delivery using a medical device can be further broken into two categories, namely, short term and long term. The short term delivery of a therapeutic agent occurs generally within a matter of seconds or minutes to a few days or weeks. The long term delivery of a therapeutic agent occurs generally within several weeks to a number of months. Typically, to achieve the long term delivery of a therapeutic agent, the therapeutic agent must be combined with a delivery agent, or otherwise formed with a physical impediment as a part of the medical device, to slow the release of the therapeutic agent.

What is desired is a coated medical device wherein the coating is applied in a manner that provides a uniform consistent coating. The coating can be a bio-absorbable delivery agent having non-inflammatory characteristics that is able to be prepared in combination with at least one therapeutic agent for the delivery of that therapeutic agent to body tissue in a controlled release manner.

In applying coatings to medical devices, such as stents and catheters, coverage and uniformity are important factors in the getting optimal performance out of the coated medical device. If a device does not have proper coverage then there may be areas on the device that do not have proper coating which can lead to all the problems typically associated with uncoated devices. Similar problems can arise when the coating is not uniform. Non-uniform coatings can cause inconsistent interactions, especially when a therapeutic agent is being delivered. Ideally, the coating should be uniform over the medical device so that dosage and interaction with tissue can be better controlled.

SUMMARY OF THE INVENTION

There is a need for an application technique for applying uniform consistent coating to an implantable medical device for therapeutic purposes. In accordance with the present invention a method and device for applying a coating to a medical device, such as a stent, balloon, or catheter, are provided that can produce uniform consistent coverage in a repeatable and controllable manner.

In accordance with a first aspect, an applicator is provided for applying a coating to a medical device, the applicator features a sheath having a first end, a second end, and a lumen between the first end and the second end, the first end being flared and having a cross-sectional area greater than a cross-sectional area of at least a portion of the lumen and wherein the sheath is sized and dimensioned to fit over the medical device providing a clearance between the sheath and the medical device for receiving a coating substance for application of the coating substance to the medical device.

In accordance with another aspect, a method is provided for preparing a coated medical device. The method involves providing a medical device onto which a coating is to be applied, providing a coating substance for application onto the medical device; and applying the coating substance to the medical device using an applicator featuring a sheath having a first end, a second end, and a lumen between the first end and the second end, the first end being flared and having a cross-sectional area greater than a cross-sectional area of at least a portion of the lumen and wherein the sheath is sized and dimensioned to fit over the medical device providing a clearance between the sheath and the medical device for receiving a coating substance for application of the coating substance to the medical device.

In accordance with certain aspects, applying the coating substance to the medical device includes placing the applicator onto the medical device; and filling the applicator with the coating substance. In certain embodiments this may also include removing the applicator from the medical device leaving a residual coating of the coating substance on the medical device. In some embodiments, the applicator is placed onto and removed from the medical device by sliding the applicator on or off the medical device.

In accordance with other aspects, applying a coating substance to the medical device includes placing the coating substance on the medical device and spreading the coating substance over the medical device by sliding the applicator over the medical device.

In accordance with certain aspects of the present invention, the method further includes curing the coating substance on the medical device to form the coating. Curing with respect to the present invention generally refers to thickening, hardening, or drying of a material brought about by heat, UV, reactive gas, or chemical means.

In accordance with some aspects, the method further includes the step of placing a protective sleeve over the medical device to protect the coating on the medical device.

In accordance with other aspects, the medical device is a stent, balloon, or catheter. In some embodiments a stent is located on an end of a catheter for deployment by the catheter.

In accordance with one aspect, a cap is provided for use in the application of a coating to a catheter. The cap features a section of tubing configured to fit on the end of the catheter to seal the lumen at the end of the catheter during the application of a coating. In some embodiments the cap is a cap stylet. The cap stylet features a stylet configured to fill a lumen of the catheter and a section of tubing attached to the stylet sized and dimensioned to be fitted on the end of the catheter to seal the lumen of the catheter.

In accordance with another aspect, a method of applying a coating to a catheter is provided. The method includes providing a catheter having a proximal end, a distal end, and a lumen between the proximal and distal ends, providing a coating substance or application onto the catheter, providing a cap configured to fit onto an end of the catheter, placing the cap onto an end of the catheter, and applying the coating substance onto the catheter, wherein, the cap prevents coating substance from penetrating the lumen at the end of the catheter. The coating substance can be applied using an applicator.

In accordance with one aspect, a system is provided for use in preparing a coated catheter, the system includes a cap stylet including a stylet configured to fill a lumen of the catheter and a section of tubing attached to the stylet sized and dimensioned to be fitted on an end of the catheter to seal the lumen of the catheter; and an applicator featuring a sheath having a first end, a second end, and a lumen between the first end and the second end, the first end being flared and having a cross-sectional area greater than a cross-sectional area of at least a portion of the lumen and wherein the sheath is sized and dimensioned to fit over the medical device providing a clearance between the sheath and the medical device for receiving a coating substance for application to the medical device. In certain embodiments the system may further include a protective sleeve configured to be place over the catheter to protect a coating on the catheter.

In accordance with another aspect, a method of coating a catheter is provided. The method includes providing a catheter having a proximal end, a distal end, and a lumen between the proximal and distal ends; providing a coating substance or application onto the catheter; providing a cap stylet configured to fit onto an end of the catheter; providing an applicator featuring a sheath having a first end, a second end, and a lumen between the first end and the second end, the first end being flared and having a cross-sectional area greater than a cross-sectional area of at least a portion of the lumen and wherein the sheath is sized and dimensioned to fit over the medical device providing a clearance between the sheath and the medical device for receiving a coating substance for application of the coating substance to the medical device configured to apply a coating to the catheter; placing the cap stylet onto an end of the catheter; and applying the coating substance onto the catheter using the applicator; wherein the cap stylet prevents coating substance from penetrating the lumen at the end of the catheter.

BRIEF DESCRIPTION OF THE DRAWINGS

The aforementioned features and advantages, and other features and aspects of the present invention, will become better understood with regard to the following description and accompanying drawings, wherein.

DETAILED DESCRIPTION

An illustrative embodiment of the present invention relates to the provision of a coating on an implantable medical device. The coating can include a bio-absorbable carrier component. In addition to the bio-absorbable carrier component, a therapeutic agent component can also be provided. However, the coating is not limited to a bio-absorbable carrier component or a therapeutic agent component. Rather, any variation of coating formed with application of a relatively liquid or fluent material that is desired for application to a medical device can be applied using the applicator and method of the present invention. The coated medical device can be implantable in a patient to affect controlled delivery of the coating to the patient, or can be for external use.

As utilized herein, the term "bio-absorbable" generally refers to having the property or characteristic of being able to penetrate the tissue of a patient's body. In certain embodiments of the present invention bio-absorption occurs through a lipophilic mechanism. The bio-absorbable substance is soluble in the phospholipid bi-layer of cells of body tissue, and therefore impacts how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes, in a manner that does not result in cellular uptake of the biodegradable substance. Biodegradation thus relates to the breaking down and distributing of a substance through the patient's body, verses the penetration of the cells of the patient's body tissue. Biodegradable substances can cause inflammatory response due to either the parent substance or those formed during breakdown, and they may or may not be absorbed by tissues.

The phrase "controlled release" generally refers to the release of a biologically active agent in a predictable manner over the time period of weeks or months, as desired and predetermined upon formation of the biologically active agent on the medical device from which it is being released. Controlled release includes the provision of an initial burst of release upon implantation, followed by the predictable release over the aforementioned time period.

With regard to the aforementioned oils, it is generally known that the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

Oil that is hydrogenated becomes a waxy solid. Attempts have been made to convert the polyunsaturated oils into a wax or solid to allow the oil to adhere to a device for a longer period of time. One such approach is known as hydrogenation, which is a chemical reaction that adds hydrogen atoms to an unsaturated fat (oil) thus saturating it and making it solid at room temperature. This reaction requires a catalyst, such as a heavy metal, and high pressure. The resultant material forms a non-crosslinked semi-solid. Hydrogenation can reduce or eliminate omega-3 fatty acids, and any therapeutic effects (both anti-inflammatory and wound healing) they offer.

In addition, some curing methods have been indicated to have detrimental effects on the therapeutic agent combined with the omega-3 fatty acid, making them partially or completely ineffective. As such, oils, and more specifically oils containing omega-3 fatty acids, have been utilized as a delivery agent for the short term uncontrolled release of a therapeutic agent, so that minimal or no curing is required. However, there are no known uses of oils containing omega-3 fatty acids for combination with a therapeutic agent in a controlled release application that makes use of the therapeutic benefits of the omega-3 fatty acids. Further, some heating of the omega-3 fatty acids to cure the oil can lessen the total therapeutic effectiveness of the omega-3 fatty acids, but not eliminate the therapeutic effectiveness. One characteristic that can remain after certain curing by heating methods is the non-inflammatory response of the tissue when exposed to the cured material. As such, an oil containing omega-3 fatty acids can be heated for curing purposes, and still maintain some or even a substantial portion of the therapeutic effectiveness of the omega-3 fatty acids. In addition, although the therapeutic agent combined with the omega-3 fatty acid and cured with the omega-3 fatty acid can be rendered partially ineffective, the portion remaining of the therapeutic agent can, in accordance with the present invention, maintain pharmacological activity and in some cases be more effective than an equivalent quantity of agent delivered with other coating delivery agents. Thus, if for example, 80% of a therapeutic agent is rendered ineffective during curing, the remaining 20% of therapeutic agent, combined with and delivered by the coating can be efficacious in treating a medical disorder, and in some cases have a relatively greater therapeutic effect than the same quantity of agent delivered with a polymeric or other type of coating.

For long term controlled release applications, polymers, as previously mentioned, have been utilized in combination with a therapeutic agent. Such a combination provides a platform for the controlled long term release of the therapeutic agent from a medical device. However, polymers have been determined to themselves cause inflammation in body tissue. Therefore, the polymers often must include at least one therapeutic agent that has an anti-inflammatory effect to counter the inflammation caused by the polymer delivery agent. In addition, patients that received a polymer-based implant must also follow a course of long term systemic anti-platelet therapy to offset the thrombogenic properties of the non-absorbable polymer. A significant percentage of patients that receive such implants are required to undergo additional medical procedures, such as surgeries (whether related follow-up surgery or non-related surgery) and are required to stop their anti-platelet therapy. This can lead to a thrombotic event, such as stroke, which can lead to death. Use of the inventive coating described herein can negate the necessity of anti-platelet therapy, and the corresponding related risks described, because there is no thrombogenic polymer reaction to the coating.

FIGS. 1 through 14, wherein like parts are designated by like reference numerals throughout, illustrate example embodiments of an applicator and corresponding method for coating a medical device, along with representative coated medical device examples. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

Figure 1:
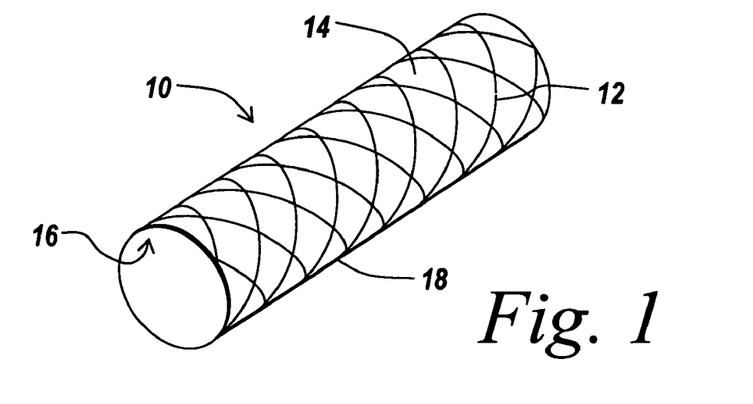
FIG. 1 is a diagrammatic illustration of a medical device, according to one embodiment of the present invention.

FIG. 1 illustrates a stent 10 in accordance with one embodiment of the present invention. The stent 10 is representative of a medical device that is suitable for having a coating applied thereon to affect a therapeutic result. The stent 10 is formed of a series of interconnected struts 12 having gaps 14 formed therebetween. The stent 10 is generally cylindrically shaped. Accordingly, the stent 10 maintains an interior surface 16 and an exterior surface 18.

One of ordinary skill in the art will appreciate that the illustrative stent 10 is merely exemplary of a number of different types of stents available in the industry. For example, the strut 12 structure can vary substantially. The material of the stent can also vary from a metal, such as stainless steel, Nitinol, nickel, tantalum, magnesium, and titanium alloys, to cobalt chromium alloy, ceramic, plastic, and polymer type materials. One of ordinary skill in the art will further appreciate that the present invention is not limited to use on stents. Instead, the present invention has application on a wide variety of medical devices. For purposes of clarity, the following description will refer to a stent as the exemplar medical device. The terms medical device and stent are interchangeable with regard to the applicability of the present invention. Accordingly, reference to one or another of the stent, or the medical device, is not intended to unduly limit the invention to the specific embodiment described.

Figure 2:
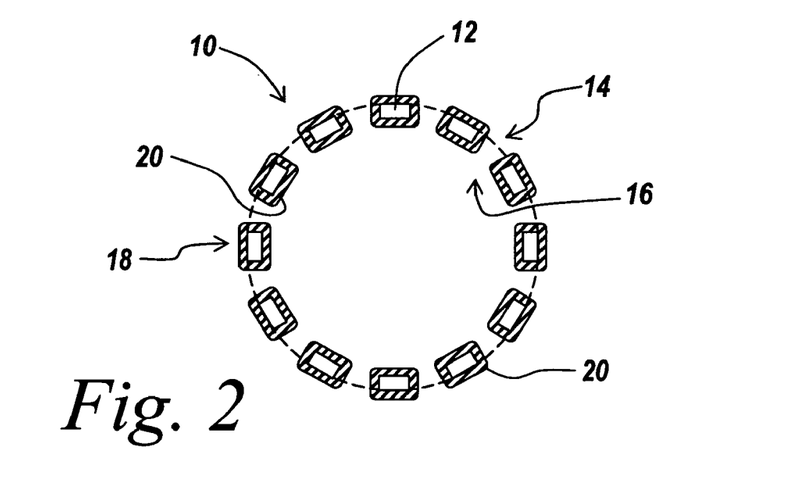
FIG. 2 is a cross-sectional view of the medical device in accordance with one aspect of the present invention.
Figure 3:
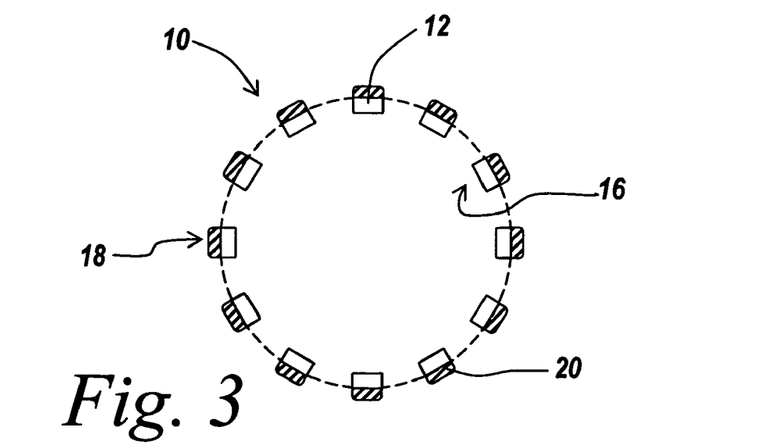
FIG. 3 is a cross-sectional view of the medical device in accordance with another aspect of the present invention.

FIG. 2 illustrates one example embodiment of the stent 10 having a coating 20 applied thereon in accordance with the present invention. FIG. 3 is likewise an alternative embodiment of the stent 10 having the coating 20 also applied thereon. The coating 20 is applied to the medical device, such as the stent 10, to provide the stent 10 with different surface properties, and also to provide a vehicle for therapeutic applications.

In FIG. 2, the coating 20 is applied on both the interior surface 16 and the exterior surface 18 of the strut 12 forming the stent 10. In other words, the coating 20 in FIG. 2 substantially encapsulates the struts 12 of the stent 10. In FIG. 3, the coating 20 is applied only on the exterior surface 18 of the stent 10, and not on the interior surface 16 of the stent 10. The coating 20 in both configurations is the same coating; the difference is merely the portion of the stent 10 that is covered by the coating 20. One of ordinary skill in the art will appreciate that the coating 20 as described throughout the Description can be applied in both manners shown in FIG. 2 and FIG. 3, in addition to other configurations such as, partially covering select portions of the stent 10 structure. All such configurations are described by the coating 20 reference.

In some instances of the resulting coated medical device, the stent 10 includes the coating 20, which is bio-absorbable. The coating 20 has a bio-absorbable carrier component, and can also include a therapeutic agent component that can also be bio-absorbable. When applied to a medical device such as a stent 10, it is often desirable for the coating to inhibit or prevent restenosis. Restenosis is a condition whereby the blood vessel experiences undesirable cellular remodeling after injury. When a stent is implanted in a blood vessel, and expanded, the stent itself may cause some injury to the blood vessel. The treated vessel typically has a lesion present which can contribute to the inflammation and extent of cellular remodeling. The end result is that the tissue has an inflammatory response to the conditions. Thus, when a stent is implanted, there is often a need for the stent to include a coating that inhibits inflammation, or is non-inflammatory, and prevents restenosis. These coatings have been provided using a number of different approaches as previously described in the Background. However, none of the prior coatings have utilized a bio-absorbable carrier component to create a bio-absorbable coating with suitable non-inflammatory properties for controlled release of a therapeutic agent.

In some instances of the resultant coated medical device, the bio-absorbable carrier component is in the form of a naturally occurring oil. An example of a naturally occurring oil is fish oil or cod liver oil. A characteristic of the naturally occurring oil is that the oil includes lipids, which contributes to the lipophilic action that is helpful in the delivery of therapeutic agents to the cells of the body tissue. In addition, the naturally occurring oil includes omega-3 fatty acids in accordance with several embodiments of the present invention. As previously described, omega-3 fatty acids and omega-6 fatty acids are known as essential fatty acids. Omega-3 fatty acids can be further characterized as eicosapentaenoic acid (EPA), docosahexanoic acid (DHA), and alpha-linolenic acid (ALA). Both EPA and DHA are known to have anti-inflammatory effects and wound healing effects within the human body.

In further detail, the term "bio-absorbable" generally refers to having the property or characteristic of being able to penetrate the tissues of a patient's body. The bio-absorbable coating contains lipids, many of which originate as triglycerides. It has previously been demonstrated that triglyceride products such as partially hydrolyzed triglycerides and fatty acid molecules can integrate into cellular membranes and enhance the solubility of drugs into the cell. Whole triglycerides are known not to enhance cellular uptake as well as partially hydrolyzed triglyceride, because it is difficult for whole triglycerides to cross cell membranes due to their relatively larger molecular size. Vitamin E compound can also integrate into cellular membranes resulting in decreased membrane fluidity and cellular uptake.

It is also known that damaged vessels undergo oxidative stress. A coating containing an antioxidant such as alpha-tocopherol may aid in preventing further damage by this mechanism.

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha-tocopherol can be used alone or in combination to provide an effective transport of a given compound to a given region or location. Both fatty acids and alpha-tocopherol are accommodated by the coating of the present invention described herein. Accordingly, fatty acids and alpha-tocopherol can be combined in differing amounts and ratios to contribute to a coating in a manner that provides control over the cellular uptake characteristics of the coating and any therapeutic agents mixed therein.

It should further be emphasized that the bio-absorbable nature of the carrier component and the resulting coating (in the instances where a bio-absorbable therapeutic agent component is utilized) results in the coating 20 being completely absorbed over time by the cells of the body tissue. There are no break down products of the coating that induce an inflammatory response. In short, the coating 20 is generally composed of fatty acids, including in some instances omega-3 fatty acids, bound to triglycerides, potentially also including a mixture of free fatty acids and vitamin E. The triglycerides are broken down by lipases (enzymes) which result in free fatty acids that can than be transported across cell membranes. Subsequently, fatty acid metabolism by the cell occurs to metabolize any substances originating with the coating. The bio-absorbable nature of the coating thus results in the coating being absorbed, leaving only an underlying delivery or other medical device structure. There is no foreign body response to the bio-absorbable carrier component, including no inflammatory response. The modification of the oils from a more liquid physical state to a more solid, but still flexible, physical state is implemented through the curing process. As the oils are cured, especially in the case of fatty acid-based oils such as fish oil, cross-links form creating a gel. As the curing process is performed over increasing time durations and/or increasing temperature conditions, more cross-links form transitioning the gel from a relatively liquid gel to a relatively solid-like, but still flexible, gel structure.

The coating can also include a therapeutic agent component. The therapeutic agent component mixes with the bio-absorbable carrier component as described later herein. The therapeutic agent component can take a number of different forms including but not limited to anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, antiseptics, proteoglycans, GAG's, gene delivery (polynucleotides), polysaccharides (e.g., heparin), anti-migratory agents, pro-healing agents, ECM/protein production inhibitors, analgesics, prodrugs, and any additional desired therapeutic agents such as those listed in Table 1 below.

TABLE #1

| CLASS | EXAMPLES |
|---|---|
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abciximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, |

TABLE #1-continued

| CLASS | EXAMPLES |
|---|---|
| | urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibition of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma - 1b, Interluekin - 10 |
| Immunosuppressive/Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |

TABLE #1-continued

| CLASS | EXAMPLES |
|---|---|
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example as described in US Patent Application Publication 2004/0235762), a rapamycin derivative (for example as described in U.S. Pat. No. 6,200,985), everolimus, seco-rapamycin, seco-everolimus, and simvastatin. Depending on the type of therapeutic agent component added to the coating, the resulting coating can be bio-absorbable if the therapeutic agent component is also bio-absorbable. As described in the Summary of the Invention, the present invention relates to coating a medical device with a coating. The coating is formed of at least two primary components, namely a bio-absorbable carrier component and a therapeutic agent component. The therapeutic agent component has some form of therapeutic or biological effect. The bio-absorbable carrier component can also have a therapeutic or biological effect. It should again be noted that the bio-absorbable carrier component is different from the conventional bio-degradable substances utilized for similar purposes. The bio-absorbable characteristic of the carrier component enables the cells of body tissue of a patient to absorb the bio-absorbable carrier component itself, rather than breaking down the carrier component into inflammatory by-products and disbursing said by-products of the component for ultimate elimination by the patient's body. Accordingly, anti-inflammatory drug dosages to the patient do not need to be increased to additionally compensate for inflammation caused by the carrier component, as is otherwise required when using polymer-based carriers that themselves cause inflammation.

It should also be noted that the present description makes use of the stent 10 as an example of a medical device that can be coated with the coating 20 of the present invention. However, the present invention is not limited to use with the stent 10. Instead, any number of other implantable medical devices can be coated in accordance with the teachings of the present invention with the described coating 20. Such medical devices include catheters, grafts, balloons, prostheses, stents, other medical device implants, and the like. Implantation refers to both temporarily implantable medical devices, as well as permanently implantable medical devices. In the instance of the example stent 10, a common requirement of stents is that they include some substance or agent that inhibits restenosis. Accordingly, the example coating 20 as described is directed toward the reduction or the elimination of restenosis. However, one of ordinary skill in the art will appreciate that the coating 20 can have other therapeutic or biological benefits. The composition of the coating 20 is simply modified or mixed in a different manner to result in a different biological effect.

Figure 4:
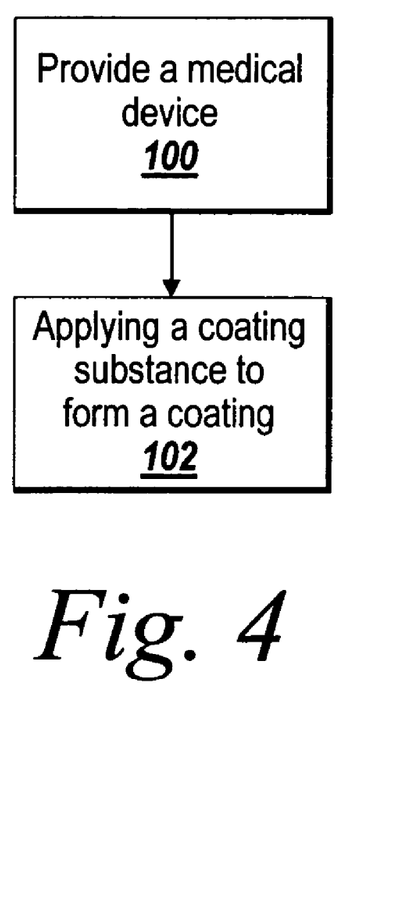
FIG. 4 is a flow chart illustrating a method of making a coated medical device, in accordance with one embodiment of the present invention.

FIG. 4 illustrates one method of making a coated medical device, in the form of the coated stent 10. The process involves providing a medical device, such as the stent 10 (step 100). A coating, such as coating 20, is then applied to the medical device (step 102). One of ordinary skill in the art will appreciate that this basic method of application of a coating to a medical device such as the stent 10 can have a number of different variations falling within the process described. Depending on the particular application, the stent 10 with the coating 20 applied thereon can be implanted after the coating 20 is applied, or additional steps such as curing, sterilization, and removal of solvent can be applied to further prepare the stent 10 and coating 20. Furthermore, if the coating 20 includes a therapeutic agent that requires some form of activation (such as UV light), such actions can be implemented accordingly.

In one embodiment of the present invention, applying the coating to the medical device involves using an applicator to apply the coating. The use of an applicator allows for application of coating having improved uniformity and coverage. An exemplary method of this can be seen in FIG. 5. The method involves providing a medical device onto which a coating is to be applied (step 202); providing a coating substance for application onto the medical device (step 204); and applying the coating substance to the medical device using an applicator (step 206). In certain embodiments, the method may further include the step of curing the coating substance to form a coating on the medical device (step 208).

Figure 6A:
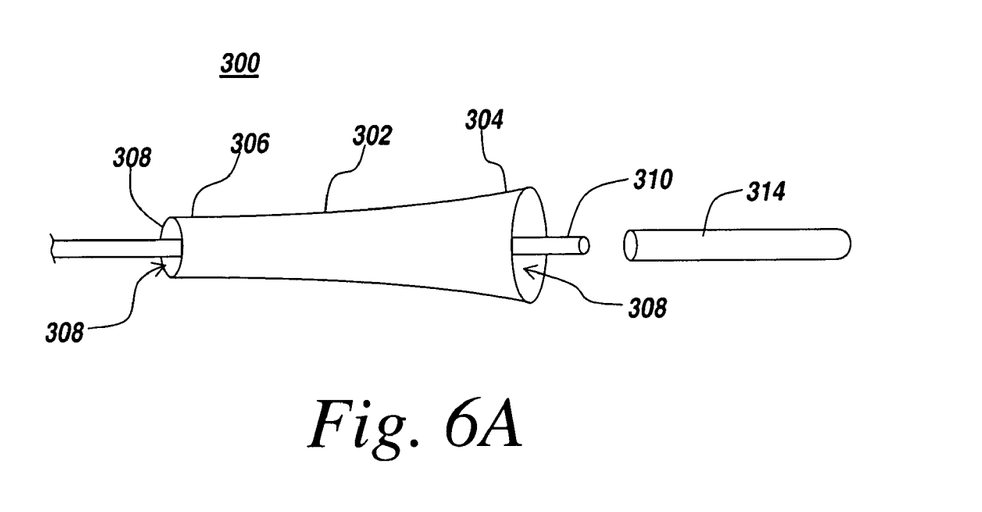
FIG. 6A is a diagrammatic illustration of an applicator in accordance with one embodiment of the present invention.
Figure 6B:
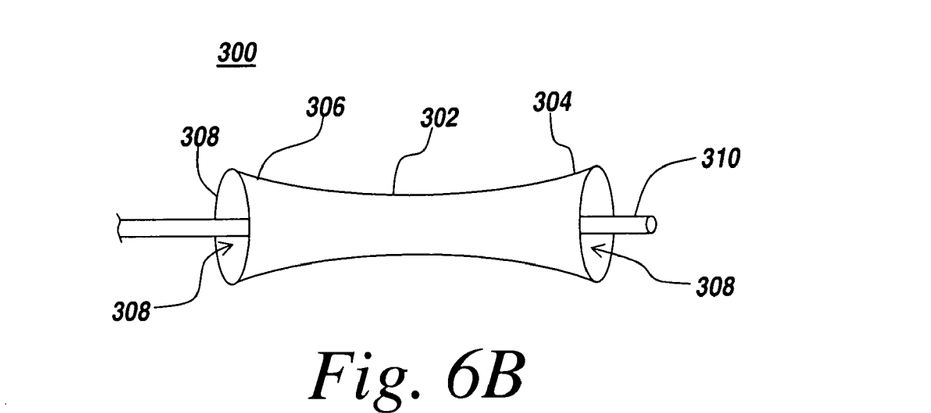
FIG. 6B is a diagrammatic illustration of an applicator in accordance with another embodiment of the present invention.

An exemplary embodiment of an applicator 300 can be seen in FIG. 6A. The applicator 300 is formed of a sheath 302 having a first end 304, a second end 306 and a lumen 308 between the first 304 and second 306 ends. The first end 304 is flared and has a cross-sectional area greater than a cross sectional area of a portion of the lumen 308. The sheath 302 is sized and dimensioned to fit over the medical device 310, while providing a clearance between the sheath 302 and the medical device 310 for receiving a coating substance for application to the medical device 310. In some embodiments, the second end 306 may also be flared and have a cross-sectional area greater than a cross-sectional area of at least a portion of the lumen 308, as can be seen in FIG. 6B. Examples of medical devices 310 on which the applicator 300 may be used include stents and catheters. In certain embodiments, a coating is applied to a stent that has been positioned on the end of a catheter. Preferably, the applicator 300 is formed of plastic but other suitable material that can be formed into the desired configuration can be used.

In the present embodiment the cross-section shape of the applicator is circular giving the applicator a funnel or trumpet like shape. Other suitable cross sectional shapes include polygonal shapes such as hexagonal, octagonal, or the like. Other possible shapes and configurations will be apparent to one skilled in the art given the benefit of this disclosure.

In use, the coating is applied by placing the applicator 300 onto the medical device 310 and then filling the applicator 300 with the coating substance. The flared nature of the first end 304 assists in providing a larger opening for receiving the coating substance and directing it onto the medical device. The coating substance may be placed into the applicator 300, for example, at flared first end 304, or be placed onto the medical device 310 directly. In certain embodiments the coating substance is delivered using metering device, such as a syringe, so that the amount of coating, and in certain cases, dosage of therapeutic agent, can be controlled.

In the present embodiment the applicator 300 is configured to slide onto the medical device 310. In other embodiments, the applicator 300 may be formed of two halves that are joined together around the medical device 310. Other possible configurations will be apparent to one skilled given the benefit of this disclosure.

In certain embodiments, after the applicator 300 has been filled with coating substance, the applicator 300 can be removed. In the present embodiment, wherein the applicator 300 is configured to slide onto the medical device 310, removing the applicator 300 is performed by sliding the applicator 300 off the medical device 310. Alternately, the coating substance may be applied directly to the medical device 310 and the applicator 300 is then slid over the medical device 310 to spread the coating substance over the medical device 310. In this embodiment, the clearance between the sheath 302 and the medical device 310 is dimensioned and sized to leave a residual coating of the coating substance on the medical device 310 as the applicator 300 is slid over the medical device 310. Preferably, the clearance is between 0.0001 to 0.1 inches. More preferably, the clearance is between 0.001 to 0.01 inches. In certain embodiments the uniformity and coverage of such a residual coating can be improved by sliding the applicator 300 over the medical device 310 with a twisting motion.

Figure 5:
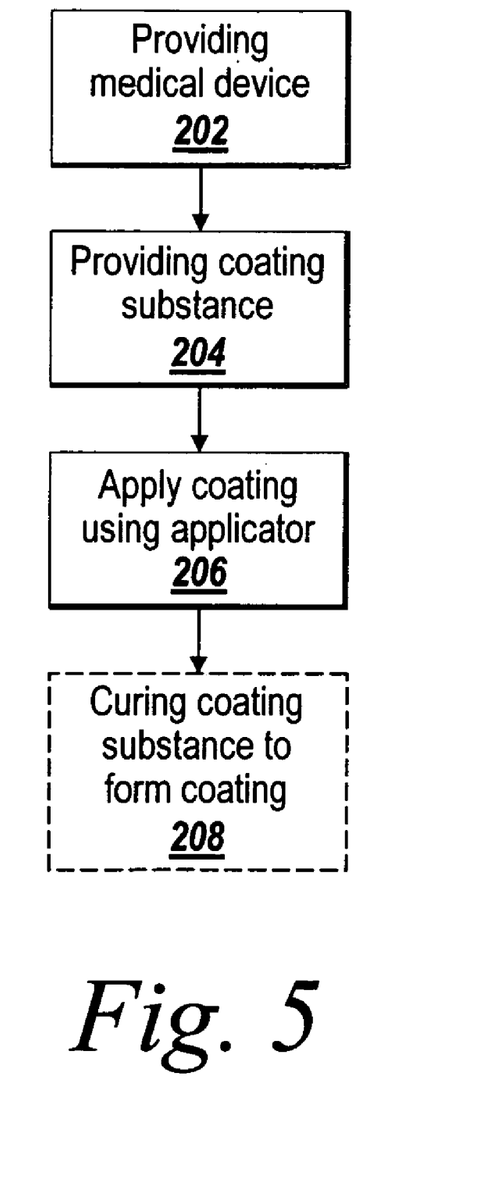
FIG. 5 is a flow chart illustrating a variation of the method of FIG. 4 using an applicator in accordance with one embodiment of the present invention.

In certain embodiments, as set forth in step 208 of FIG. 5, once the coating substance has been applied to the medical device, the coating substance is cured to form the coating on the medical device. Curing can be performed after the applicator has been removed, or with the applicator still in place over the medical device. Curing with respect to the present invention generally refers to thickening, hardening, or drying of a material brought about by heat, UV, reactive gases, or chemical means.

In some embodiments, once the coating has been formed on the medical device 310, a protective sleeve 314 is placed over the medical device 310 to protect the coating on the medical device 310 during further handling. In an exemplary embodiment, the protective sleeve 314 is formed of plastic, and sized and dimensioned to fit over the medical device 310. Other suitable implementations will be apparent to one skilled in the art given the benefit of this disclosure.

In certain embodiments wherein a coating is being applied to a catheter, a cap, such as cap stylet, may be used when applying the coating substance. When placed on the end of a catheter, the cap prevents coating substance from penetrating the lumen at the end of the catheter. An exemplary embodiment of such a method can be seen in FIG. 7. In this embodiment, the method involves providing a catheter onto which a coating is to be applied (step 402), providing a coating substance for application onto the catheter (step 404), providing a cap configured to fit onto an end of the catheter (step 406); placing the cap onto an end of the catheter (step 408), and applying the coating substance onto the catheter (step 410).

The cap comprises a section of tubing configured to fit on the end of the catheter to seal the lumen at the end of the catheter during the application of a coating. An exemplary embodiment of a cap and its interaction with a catheter can be seen in FIG. 8. In this embodiment the cap is a cap stylet 500. The catheter 520 has a proximal end (not shown), a distal end 522, and a lumen 524 between the proximal and distal ends. The cap stylet 500 features a stylet 502 configured to fill the lumen 524 of the catheter 520; and a section of tubing 504 attached to the stylet 502 sized and dimensioned to be fitted on the end of the catheter 520 to seal the lumen 524 of the catheter 520. In certain embodiments, the section of tubing 504 is sized to pinch fit on the end of a catheter 520. Alternately, the cap can snap or interference fit on the end of the catheter. When placed on the end of a catheter 520, the cap stylet 500 prevents the coating substance from wicking into the lumen 524 at the end of the catheter 520 as a coating is applied. If the coating substance gets into the lumen 524 it could create an obstruction that may adversely effect the operation of the catheter 520. Preferably, the cap stylet 500 is placed on the distal end 522 of the catheter 520, which is to be inserted into a patient, and is thus coated. In certain embodiments wherein the whole catheter is to be coated, a cap stylet 500 can be placed on each end of the catheter 520.

Figure 7:
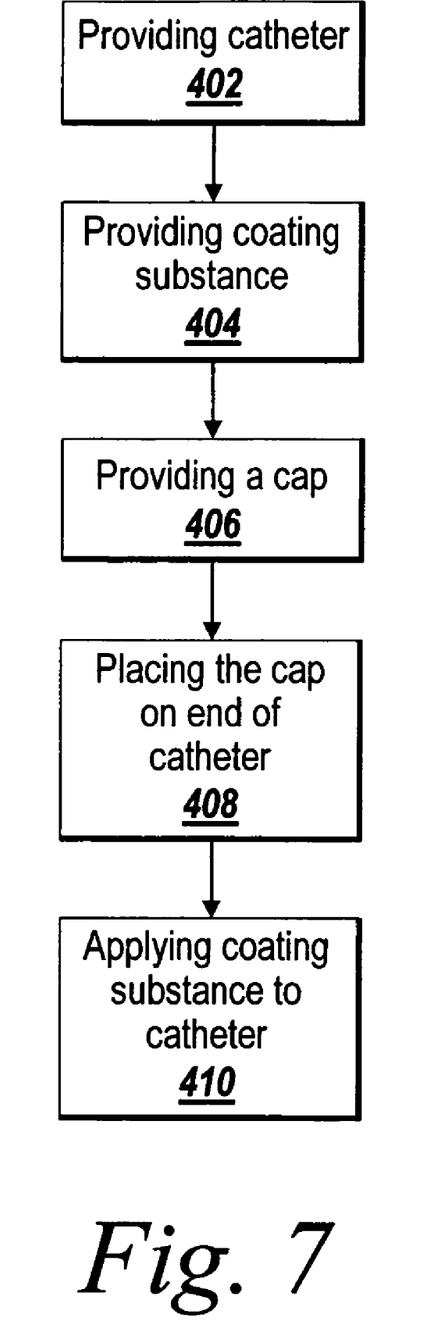
FIG. 7 is a flow chart illustrating a variation of the method of FIG. 4 using a cap stylet in accordance with one embodiment of the present invention.

Once the cap, in this case a cap stylet 500, has been placed on the end of the catheter 520, the coating can then be applied to the catheter (step 410 of FIG. 7). In certain embodiments this involves using an applicator as set forth above. The coating may also be applied by dip coating, spray coating, printing, wiping, electrostatic coating, brushing, painting or any means suitable for applying the coating substance.

Figure 8:
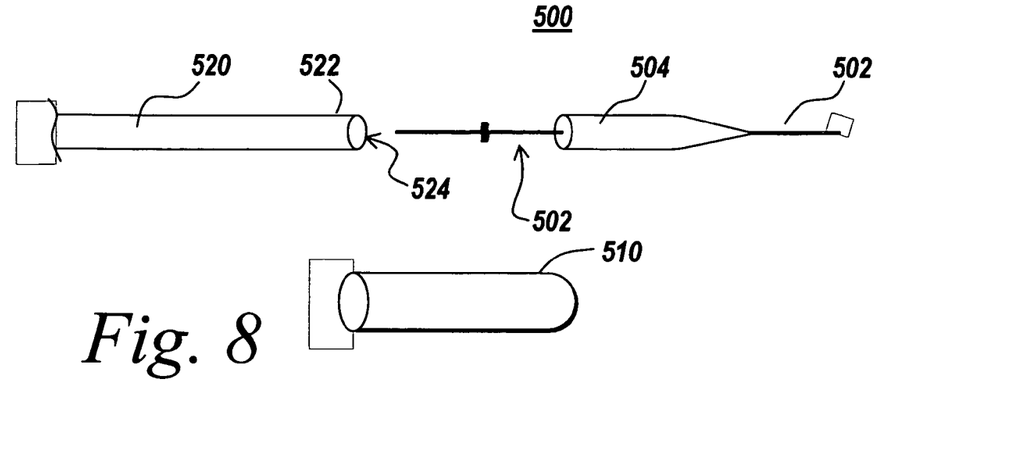
FIG. 8 is a diagrammatic illustration of a cap stylet in accordance with one embodiment of the present invention.

Once the coating substance has been applied, the coating substance can then be cured as discussed above. Likewise, in some embodiments a protective sleeve 510 may be placed on the catheter 520 to protect the coating.

Figure 9:
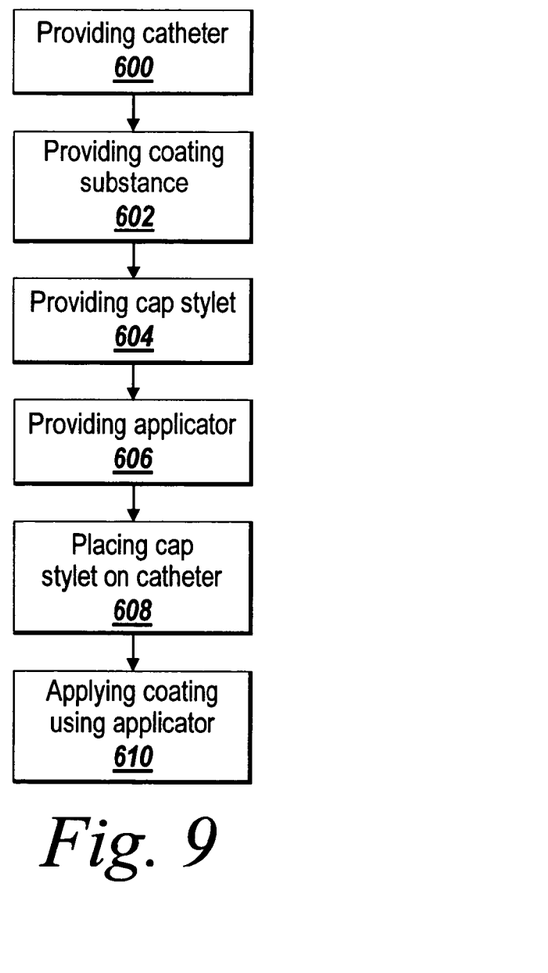
FIG. 9 is a flow chart illustrating a method of applying a coating to a catheter using an applicator and cap stylet in accordance with one embodiment of the present invention.

Another exemplary embodiment of a method, wherein an applicator and a cap stylet are used in forming a coating on a catheter, can bee seen in FIG. 9. In this embodiment, the method includes providing a catheter (step 600), providing the coating substance for application onto the catheter (step 602), providing a cap stylet configured to fit onto an end of the catheter (step 604), providing an applicator configured to apply a coating to the catheter (step 606), placing the cap stylet onto an end of the catheter (step 608) and applying the coating substance onto the catheter using the applicator (step 610).

Figure 10:
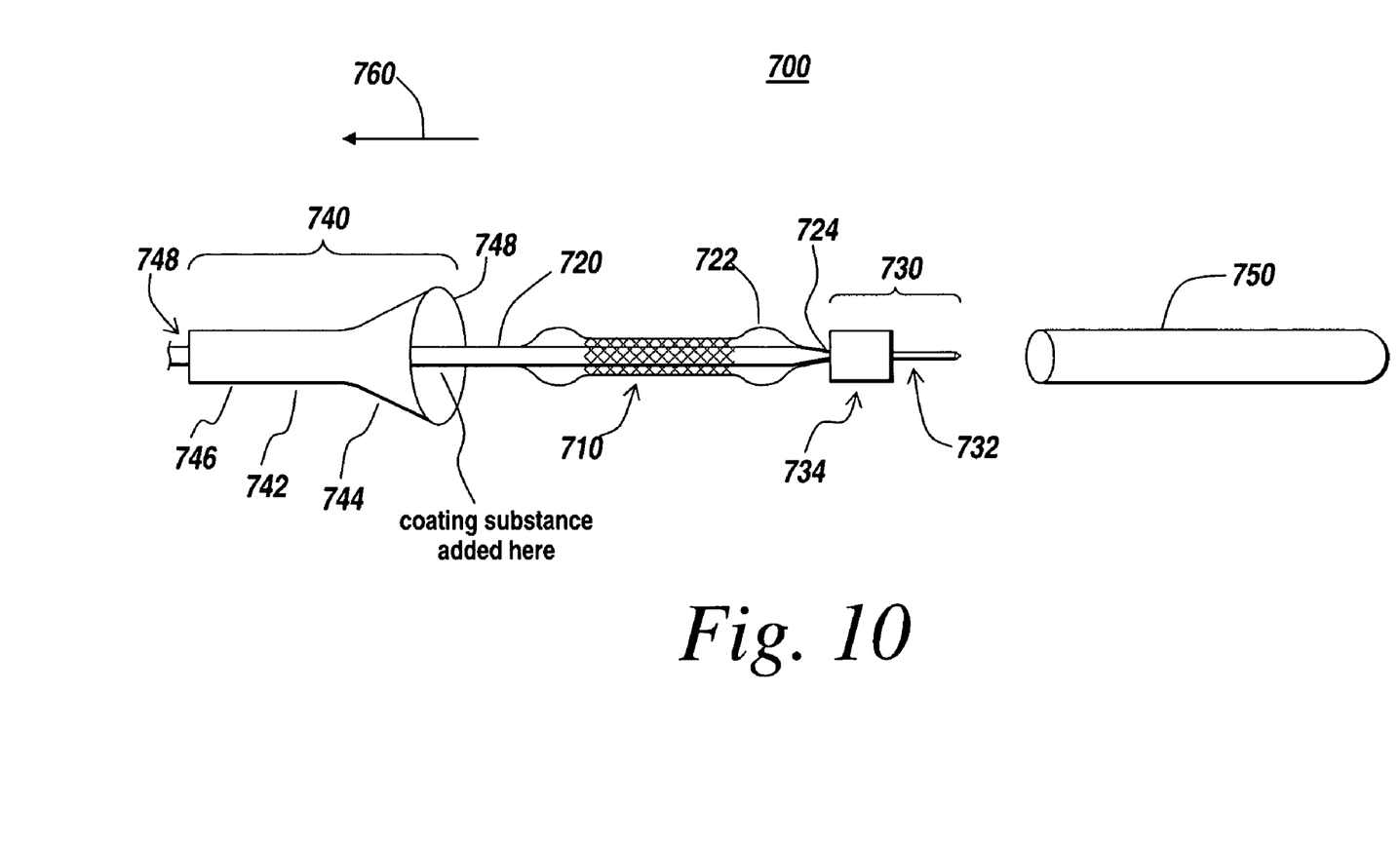
FIG. 10 is a diagrammatic illustration of the interaction of a catheter, applicator, and cap stylet in accordance with one embodiment of the present invention.

The methodology of FIG. 9 may be better understood if viewed in conjunction with the exemplary embodiment of FIG. 10 of a system 700 for applying a coating to a medical device. In this instance, a catheter 720 has a stent 710 pre-positioned on the distal end 722 of the catheter implantation in a patient. A cap stylet 730 is placed unto the distal end 722 of the catheter 720. The cap stylet 730 features a stylet 732 configured to fill a lumen 724 of the catheter 720, and a section of tubing 734 attached to the stylet 732 sized and dimensioned to be fitted on an end of the catheter 720 to seal the lumen 724 of the catheter 720. An applicator 740 is then slid onto the catheter 720 beyond the stent 710. The applicator 740 features a sheath 742 having a first end 744, a second end 746 and a lumen 748 between the first 744 and second 746 ends. The first end 744 is flared and has a cross-sectional area greater than a cross-sectional area of at least a portion of the lumen 748. The sheath 742 is sized and dimensioned to fit over the catheter 720, providing a clearance between the sheath 742 and the catheter 720 for receiving a coating substance for application to the catheter. The coating substance is then applied. In this embodiment, the applicator 740 is filled with coating substance at the flared first end 744 using a metering device, such as a syringe, to ensure the proper amount of coating substance is applied. Alternately, the coating substance may be applied directly to the catheter 720. The applicator 740 is then slid off the catheter 720 over the stent 710 and cap stylet 730 in the direction of arrow 760 using a twisting motion. The clearance between the sheath 742 and the catheter 720 is sized and dimensioned to leave a residual coating of the coating substance as the applicator 740 is slid over the catheter 720.

In certain embodiments, once the coating substance has been applied, the coating substance may be cured as discussed above. Likewise, a protective sleeve 750 can be placed over the catheter 720 and stent 710 to protect the coating during further handling.

Figure 11:
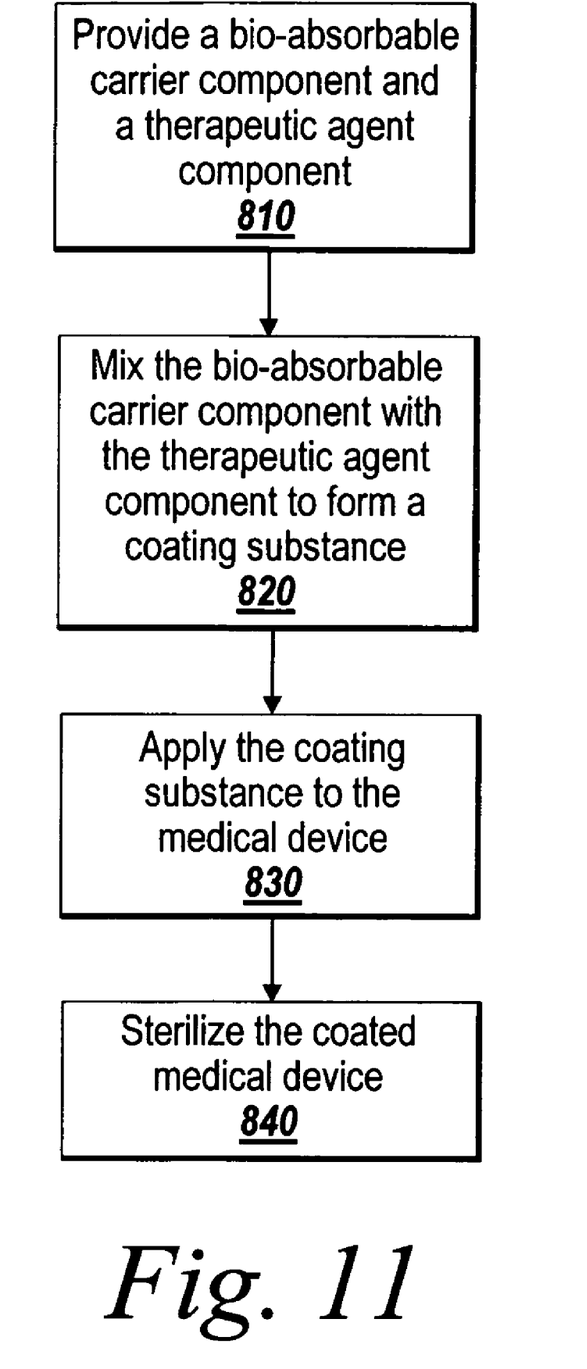
FIG. 11 is a flow chart illustrating a variation of the method of FIG. 4, in accordance with one embodiment of the present invention.

FIG. 11 is a flowchart illustrating another example implementation of the method of FIG. 4. In accordance with the steps illustrated in FIG. 11, a bio-absorbable carrier component is provided along with a therapeutic agent component (step 810). The provision of the bio-absorbable carrier component and the provision of the therapeutic agent component can occur individually, or in combination, and can occur in any order or simultaneously. The bio-absorbable carrier component is mixed with the therapeutic agent component (or vice versa) to form a coating substance (step 820). The coating substance is applied to the medical device, such as a stent or catheter, to form the coating (step 830). The coated medical device is then sterilized using any number of different sterilization processes (step 840). For example, sterilization can be implemented utilizing ethylene oxide, gamma radiation, E beam, steam, gas plasma, or vaporized hydrogen peroxide. One of ordinary skill in the art will appreciate that other sterilization processes can also be applied, and that those listed herein are merely examples of sterilization processes that result in a sterilization of the coated stent, preferably without having a detrimental effect on the coating 20.

Figure 12:
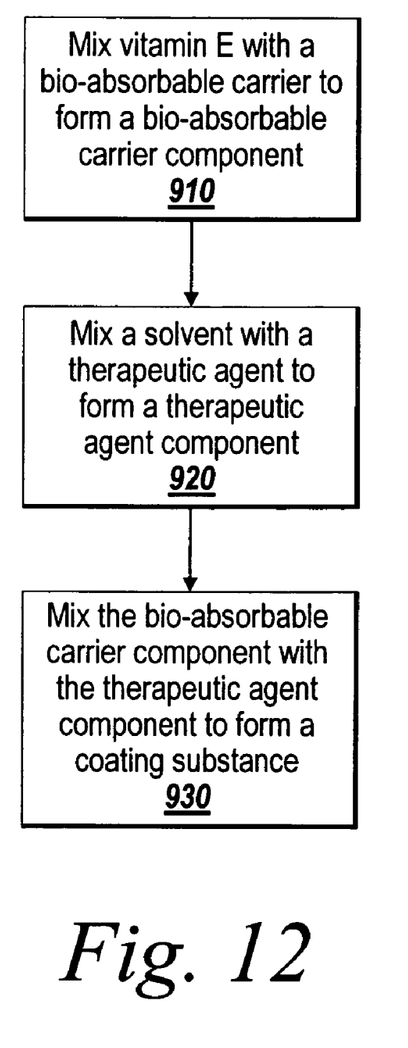
FIG. 12 is a flow chart illustrating another variation of the method of FIG. 4, in accordance with one embodiment of the present invention.
Figure 13:
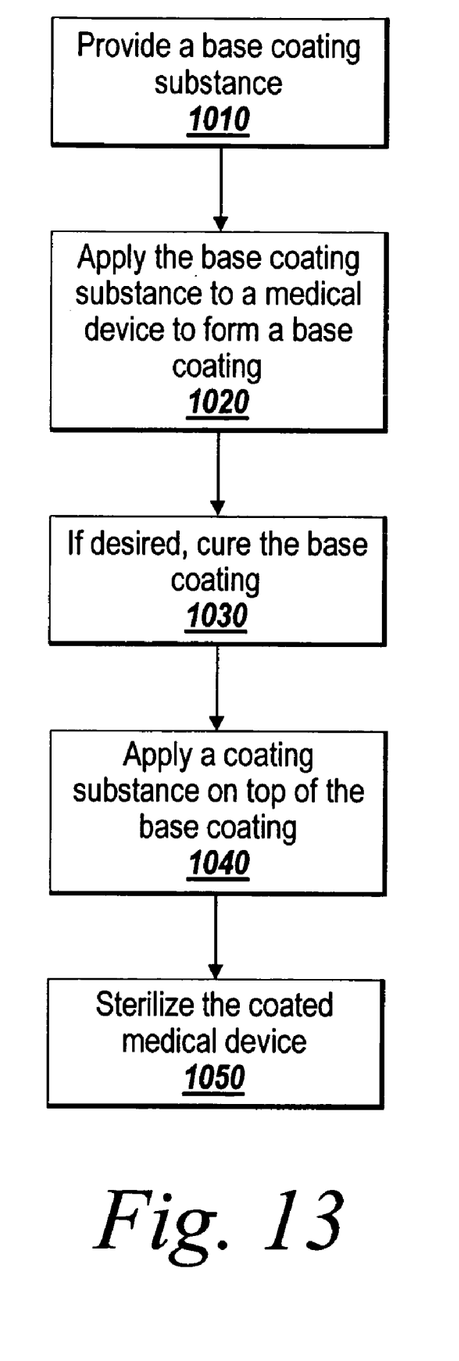
FIG. 13 is a flow chart illustrating another variation of the method of FIG. 4, in accordance with one embodiment of the present invention.

The formation of the bio-absorbable carrier component and the therapeutic agent component can be done in accordance with different methods. FIG. 12 is a flow chart illustrating one example method for forming each of the components. Vitamin E is mixed with a bio-absorbable carrier to form a bio-absorbable carrier component (step 910). A solvent is mixed with a therapeutic agent to form a therapeutic agent component (step 920). The solvent can be chosen from a number of different alternatives, including ethanol or N-Methyl-2-Pyrrolidone (NMP). The bio-absorbable carrier component is then mixed with the therapeutic agent component to form the coating substance (step 930). The solvent can then be removed with vacuum or heat. It should be noted that the preparation of the bio-absorbable carrier component and the therapeutic agent component can be done in either order, or substantially simultaneously. Additionally, in an alternative approach, the solvent can be omitted altogether.

Figure 14:
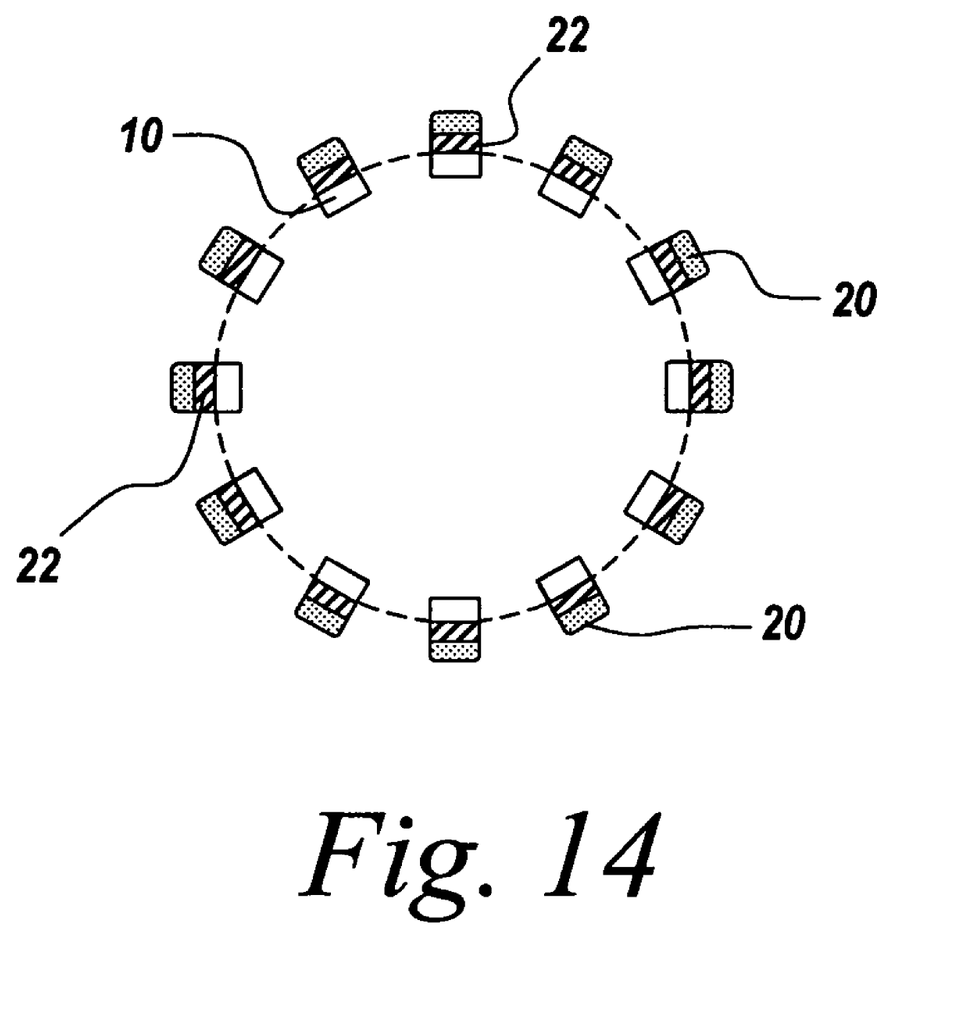
FIG. 14 is a diagrammatic illustration of a coated medical device in accordance with one embodiment of the present invention.

In accordance with another technique, a surface preparation or pre-treatment 22, as shown in FIG. 14, is provided on a stent 10. More specifically and in reference to the flowchart of FIG. 13, a pre-treatment substance or base coating is first provided (step 1010). The pre-treatment substance or base coating is applied to a medical device, such as the stent 10, to prepare the medical device surface for application of the coating (step 1020). If desired, the pre-treatment or base coating 22 is cured (step 1030). Curing methods can include processes such as application of UV light, heat, reactive gases, or chemical means to cure the pre-treatment 22. A coating substance is then applied on top of the pre-treatment 22 (step 1040). The coated medical device is then sterilized using any number of sterilization processes as previously mentioned (step 1050).

FIG. 14 illustrates the stent 10 having two coatings, specifically, the pre-treatment 22 and the coating 20. The pre-treatment 22 serves as a base or primer for the coating 20. The coating 20 conforms and adheres better to the pre-treatment 22 versus directly to the stent 10, especially if the coating 20 is not heat or UV cured. The pre-treatment can be formed of a number of different materials or substances. In accordance with one example embodiment of the present invention, the pre-treatment is formed of a bio-absorbable substance, such as a naturally occurring oil (e.g., fish oil). The bio-absorbable nature of the pre-treatment 22 results in the pre-treatment 22 ultimately being absorbed by the cells of the body tissue after the coating 20 has been absorbed.

It has been previously mentioned that curing of substances such as fish oil can reduce or eliminate some of the therapeutic benefits of the omega-3 fatty acids, including anti-inflammatory properties and healing properties. However, if the coating 20 contains the bio-absorbable carrier component formed of the oil having the therapeutic benefits, the pre-treatment 22 can be cured to better adhere the pre-treatment 22 to the stent 10, without losing all of the therapeutic benefits resident in the pre-treatment 22, or in the subsequently applied coating 20. Furthermore, the cured pre-treatment 22 provides better adhesion for the coating 20 relative to when the coating 20 is applied directly to the stent 10 surface. In addition, the pre-treatment 22, despite being cured, remains bio-absorbable, like the coating 20.

The pre-treatment 22 can be applied to both the interior surface 16 and the exterior surface 18 of the stent 10, if desired, or to one or the other of the interior surface 16 and the exterior surface 18. Furthermore, the pre-treatment 22 can be applied to only portions of the surfaces 16 and 18, or to the entire surface, if desired.

The application of the coating to the medical device can take place in a manufacturing-type facility and subsequently shipped and/or stored for later use. Alternatively, the coating can be applied to the medical device just prior to implantation in the patient. The process utilized to prepare the medical device will vary according to the particular embodiment desired. In the case of the coating being applied in a manufacturing-type facility, the medical device is provided with the coating and subsequently sterilized in accordance with any of the methods provided herein, and/or any equivalents. The medical device is then packaged in a sterile environment and shipped or stored for later use. When use of the medical device is desired, the medical device is removed from the packaging and implanted in accordance with its specific design.

In the instance of the coating being applied just prior to implantation, the medical device can be prepared in advance. The medical device, for example, can be sterilized and packaged in a sterile environment for later use. When use of the medical device is desired, the medical device is removed from the packaging, and the coating substance is applied to result in the coating resident on the medical device.

The present invention provides methods and devices for applying a coating to medical devices such as a stent. The methods and devices of the present invention provide a means for applying a coating that provides improved uniformity and coverage in a repeatable and controlled manner. The methods and devices also provide increased consistency in coating from device to device. This in turn allows for greater control of dosage of the bio-absorbable carrier and therapeutic agent.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

What is claimed is:

1. An applicator for applying a coating to a medical device, the applicator comprising:
   a sheath having a first end, a second end, and a lumen between the first end and the second end, the first end being flared outwardly from a central axis of the sheath and having a cross-sectional area greater than a cross-sectional area of at least a portion of the lumen;
   wherein the sheath is sized and dimensioned to fit over the medical device, at least a portion of the sheath provides a clearance of about 0.0001 to 0.1 inches between the sheath and the medical device for receiving a coating substance that is not the sheath for application of the coating substance to the medical device, wherein the clearance between the sheath and the medical device is sized and dimensioned to leave the coating substance on the medical device as the sheath is slid off over the medical device after the application of the coating substance to the medical device; and wherein the size and dimension of the sheath is determined based upon a size and dimension of the medical device receiving the coating.

2. The applicator of claim 1 wherein the sheath receives the coating substance at the flared first end of the sheath.

3. The applicator of claim 1 wherein the second end is flared and has a cross sectional area greater than at least a portion of the lumen.

4. The applicator of claim 1 wherein the sheath is sized and dimensioned to fit over a stent.

5. The applicator of claim 1 wherein the sheath is sized and dimensioned to fit over a catheter.

6. The applicator of claim 1 wherein the sheath is sized and dimensioned to fit over a catheter balloon.

7. The applicator of claim 1 wherein the cross-sectional shape of the applicator is circular.

8. The applicator of claim 1 wherein the cross-sectional shape of the applicator is polygonal.

9. The applicator of claim 1 wherein the clearance is in a range between 0.001 to 0.01 inches.

10. A system for use in preparing a coated catheter, the system comprising:

a cap sized and dimensioned to be fitted on an end of the catheter to seal the lumen of the catheter; and an applicator comprising a sheath having a first end, a second end, and a lumen between the first end and the second end, the first end being flared and having a cross-sectional area greater than a cross-sectional area of at least a portion of the lumen;

wherein the sheath is sized and dimensioned to fit over the catheter providing a clearance between the sheath and the catheter for receiving a coating substance that is not the sheath for application to the catheter, and wherein the clearance between the sheath and the catheter is sized and dimensioned to leave the coating substance on the catheter as the sheath is slid off over the catheter after the application of the coating substance to the catheter.

11. The system of claim 10 further comprising a protective sleeve configured to be placed over the catheter to protect a coating on the catheter.

12. The system of claim 10, wherein the cap comprises a stylet configured to fill a lumen of the catheter and a section of tubing attached to the stylet, the tubing sized and dimensioned to be fitted on an end of the catheter to seal the lumen of the catheter.

13. A system for applying a coating to a medical device, the system comprising:

an applicator having a first end, a second end, and a lumen between the first end and the second end, the first end being flared outwardly from a central axis of the applicator and having a cross-sectional area greater than a cross-sectional area of at least a portion of the lumen; and a medical device, wherein the applicator is sized and dimensioned to fit over the medical device, at least a portion of the applicator provides a clearance of about 0.0001 to 0.1 inches between the applicator and the medical device for receiving a coating substance that is not the sheath for application of the coating substance to the medical device, wherein the clearance between the applicator and the medical device is sized and dimensioned to leave the coating substance on the medical device as the applicator is slid off over the medical device after the application of the coating substance to the medical device, and wherein the size and dimension of the applicator is determined based upon a size and dimension of the medical device receiving the coating.

\* \* \* \* \*